US009898914B2

(12) United States Patent
Von Chossy et al.
(10) Patent No.: US 9,898,914 B2
(45) Date of Patent: Feb. 20, 2018

(54) TECHNOLOGY FOR DETECTING A FALL OF A PERSON

(71) Applicants: Thomas Von Chossy, Munich (DE); Henning Marchfeld, Strasslach-Dingharting (DE)

(72) Inventors: Thomas Von Chossy, Munich (DE); Henning Marchfeld, Strasslach-Dingharting (DE)

( * ) Notice: Subject to any disclaimer, the term of this patent is extended or adjusted under 35 U.S.C. 154(b) by 0 days.

(21) Appl. No.: 15/119,360

(22) PCT Filed: Jan. 15, 2015

(86) PCT No.: PCT/EP2015/050655
§ 371 (c)(1),
(2) Date: Aug. 16, 2016

(87) PCT Pub. No.: WO2015/121018
PCT Pub. Date: Aug. 20, 2015

(65) Prior Publication Data
US 2017/0061762 A1 Mar. 2, 2017

(30) Foreign Application Priority Data
Feb. 17, 2014 (DE) ........................ 10 2014 002 124

(51) Int. Cl.
*A61B 5/11* (2006.01)
*G08B 21/04* (2006.01)
*G08B 29/18* (2006.01)

(52) U.S. Cl.
CPC ....... *G08B 21/043* (2013.01); *G08B 21/0446* (2013.01); *G08B 21/0453* (2013.01); *G08B 29/185* (2013.01)

(58) Field of Classification Search
CPC .................................................... A61B 5/1117
(Continued)

(56) References Cited

U.S. PATENT DOCUMENTS

2003/0153836 A1 8/2003 Gagnadre et al.
2013/0162423 A1* 6/2013 Rowe .................... A61B 5/1113 340/501
2015/0025817 A1* 1/2015 Ten Kate .............. A61B 5/1117 702/50

FOREIGN PATENT DOCUMENTS

DE 102008049750 A1 4/2010
EP 1575010 A1 9/2005
WO 2004/114245 A1 12/2004

OTHER PUBLICATIONS

Federico Bianchi, Stephen J. Redmond, Michael R. Narayanan, Sergio Cerutti, Nigel H. Lovell, "Barometric Pressure and Triaxial Accelerometry-Based Falls Event Detection", IEEE Transactions on Neural Systems and Rehabilitation Engineering, vol. 18, No. 6, pp. 619-627, Dec. 2010, New York, NY, US.
(Continued)

*Primary Examiner* — Kevin Kim
(74) *Attorney, Agent, or Firm* — Straub & Straub; Michael P. Straub; Stephen T. Straub

(57) ABSTRACT

A technology for detecting a fall of a person is provided. A corresponding device (100) comprises an interface (102) which is designed for capturing a time-dependent air pressure signal (600) that is determined by means of at least one air pressure sensor (104, 106) worn on the body of the person. The device (100) also comprises an evaluation unit (108) which is designed for determining a fall height (λ) with respect to an evaluation time ($t_e$) by means of a window-based signal analysis of the time-dependent air-pressure signal. The window-based signal analysis includes a first time window (702) before the evaluation time and a second time window (704), which does not overlap with the first time window, after the evaluation time. The fall height is determined from a difference between a first filter value that is computed based on the time-dependent air pressure
(Continued)

400 signal in the first time window, and a second filter value that is computed based on the time-dependent air pressure signal in the second time window.

18 Claims, 6 Drawing Sheets

(58) Field of Classification Search
USPC ....................................................... 340/573.7
See application file for complete search history.

(56) References Cited

OTHER PUBLICATIONS

Jingjing Wang, Stephen J. Redmond, Matteo Voleno, Michael R. Narayanan, Ning Wang, Sergio Cerutti, Nigel H. Lovell, "Energy Expenditure Estimation During Normal Ambulation Using Triaxial Accelerometry and Barometric Pressure", Physiological Measurement, Institute of Physics Publishing, vol. 33 No. 11, pp. 1811-1830, Oct. 2012, Bristol, GB.
International Search Report and transmittal from PCT/EP/2015/050655, dated Apr. 15, 2015, in German (13 pages).

* cited by examiner

400

TECHNOLOGY FOR DETECTING A FALL OF A PERSON

TECHNICAL FIELD

The present invention relates to a technology for detecting a fall of a person. In particular, devices and methods for recognizing falls by means of at least one air pressure sensor are disclosed.

TECHNICAL BACKGROUND

Groups of persons with increased risk of falls, for example workers on tread surfaces or ladders, firefighting personnel, forestry workers, miners, hospital and nursing care patients, persons with epilepsy, or elderly persons living alone, may receive assistance in the event of a fall when they are monitored for whether they have fallen. The fall may injure persons so severely that they are no longer able to free themselves from an emergency situation or make an emergency call by their own efforts. In addition, a fall without injuries may be an indication of urgent need of treatment, for example in the event of unconsciousness.

Document EP 1 642 248 A1 describes a system for recognizing falls. A system component having a pressure sensor and a motion sensor is worn on the wrist. A second pressure sensor for measuring the air pressure in the dwelling is situated in a base station which receives the air pressure data of the wearable system component.

Document DE 10 2008 049 750 A1 describes a method for recognizing a fall of a person, based on at least one air pressure sensor. As an alternative to adjusting the air pressure sensor worn on the body of the person to a comparative pressure sensor, the option is mentioned of recognizing a fall by evaluating the measured value of the air pressure sensor as a function of time. The expected change in the measured values over time defines a "pattern." Measured values of the air pressure sensor are evaluated by means of conventional pattern recognition methods.

In conventional methods, falls without a preprogrammed pattern profile may go undetected. Conversely, variations in the weather pattern have a significant influence on the profile of the local air pressure over time, independently of a movement of the person. Even opening windows or doors may bring about numerous pressure gradients, which may trigger a false alarm if they happen to resemble a preprogrammed pattern.

SUMMARY OF THE INVENTION

The object of the present invention, therefore, is to provide a technology for reliably recognizing a fall, regardless of details of the temporal profile of a fall.

According to one aspect, a device for detecting a fall of a person is provided. The device comprises an interface which is designed for capturing a time-dependent air pressure signal that is determined by means of at least one air pressure sensor worn on the body of the person, and an evaluation unit which is designed for determining a fall height with respect to an evaluation time by means of a window-based signal analysis of the time-dependent air pressure signal, the window-based signal analysis including a first time window before the evaluation time and a second time window, which does not overlap with the first time window, after the evaluation time, and the fall height being determined from a difference between a first filter value that is computed based on the time-dependent air pressure signal in the first time window, and a second filter value that is computed based on the time-dependent air pressure signal in the second time window.

Exemplary embodiments of the device may numerically determine the fall height, and optionally an estimation error of the fall height, of a fall that has taken place between the time windows by comparing the filter values from the disjoint first and second time windows. The determination may take place, for example, without relying on specific profile patterns of the fall. The determined fall height, optionally in conjunction with the estimation error, may be the basis for an alarm signal. The estimation error may be a standard deviation.

The air pressure signal may include a difference between the at least one air pressure sensor worn on the body and at least one reference air pressure sensor.

The reference air pressure sensor may be worn by the person at a body position that is different from the worn air pressure sensor. Alternatively or in combination, the interface may capture signals of one or more stationary reference air pressure sensors. For this purpose, the interface may provide a wireless interface with the stationary air pressure sensor.

The air pressure signal may be periodically sampled. The first time window may be temporally separate from the second time window by at least one sampling period. A time interval between the first time window and the second time window may be shorter than a total duration of the first time window and the second time window.

The determination of the fall height, and optionally the estimation error, may disregard the time-dependent air pressure signal between the first time window and the second time window.

A third time window may be present between the first time window and the second time window. The fall may take place entirely in the third time window. The first time window may include a movement of the person before the fall. The second time window may include an immobile position of the person after the fall.

The first filter value and/or the second filter value may be an average value of the time-dependent air pressure signal. The average value may comprise an unweighted arithmetic mean, a weighted arithmetic mean, and/or a median.

The computation of the first filter value and/or of the second filter value may compensate for a time dependency of the time-dependent air pressure signal. The air pressure signal may be corrected for a trend, for example a weather trend. The progression of the trend may be longer than the fall or the time interval between the first time window and the second time window. The compensation may take place prior to determining the fall height, or may take place in the course of the determination, for example during the computation of the first filter value and/or the second filter value.

The time dependencies for the first time window ($F_1(t)$) and for the second time window ($F_2(t)$) may each be compensated for independently of one another. In the first time window, the first time dependency $F_1(t)$ may be fitted to the time-dependent air pressure signal. In the second time window, the second time dependency $F_2(t)$ may be fitted to the time-dependent air pressure signal, the fall height being determined from the difference between the first time dependency $F_1(t_{1,max})$ at the end time $t_{1,max}$ of the first time window, and the second time dependency $F_2(t_{2,min})$ at the start time $t_{2,min}$ of the second time window.

The first time dependency $F_1(t)$ may be a zero-, first-, or second-order polynomial in time. The second time dependency $F_2(t)$ may be a zero-, first-, or second-order polynomial in time.

Alternatively, for the first time window and for the second time window the same time dependency F(t) may be compensated for. In the first time window, the time dependency F(t), having a first time-independent offset value $C_1$ as a fit parameter, may be fitted to the time-dependent air pressure signal. In the second time window, the same time dependency F(t), having a second time-independent offset value $C_2$ as a fit parameter, may be fitted to the time-dependent air pressure signal. The fall height may be determined from the difference between the first offset value and the second offset value.

The time dependency F(t) may be a linear and/or quadratic function of time. The time dependency F(t) may correspond to a component of the time-dependent air pressure signal (caused, for example, by the variation in air pressure due to weather). The time dependency F(t) may be independent of a fall. A uniform time dependency F(t) may be present in the atmospheric pressure before and after a fall. The definition area of the function F(t) may include the first time window and the second time window.

The time-dependent air pressure signal may include a sequence of measured values associated in each case with a measuring time. The fall height may be determined with respect to a plurality of evaluation times. The evaluation time, the first time window, and/or the second time window may be incrementally shifted by a measuring time of the sequence to later points in time. The fall height, and optionally the estimation error of the fall height, may be determined for each of the evaluation times.

The first time window may be situated entirely before the second time window chronologically. The end time of the first time window may be situated prior to the start time of the second time window, by a time period that is predefined for all evaluation steps. The first time window may include only measuring times of the sequence which are situated prior to the points in time of the second time window.

A start time of the second time window and/or an end time of the first time window may each be shifted by a point in time in the sequence. The evaluation time may be equal to the end time of the first time window, or may be situated between the end time of the first time window and the start time of the second time window. The length of the second time window during the signal analysis may be equal to each of the evaluation times.

For each of the evaluation times, it may be checked whether the determined fall height exceeds a first significance criterion, for example according to $\lambda > s_1$. The first significance criterion may be two times or three times the estimation error.

For each of the evaluation times, it may be checked whether the difference between the determined fall height and a height threshold value exceeds a second significance criterion, for example according to $\lambda - \lambda_{SW} > s_2$. The second significance criterion may be two times or three times the estimation error.

An alarm state may be set in the event that the second significance criterion is exceeded.

The device may also include a trigger unit which is designed for outputting an alarm signal. The alarm signal may be output when, in the alarm state, a fit of the time-dependent air pressure signal in the second time window exceeds a predefined quality criterion. After an acoustic pre-alarm, and optionally after the absence of a user confirmation, the trigger unit transmits an alarm signal, for example by calling a preprogrammed emergency number via a landline or mobile communications network.

For each evaluation time, the first time window may be incrementally extended toward earlier measuring times. The extension may be ended when a maximum length of the first time window is reached. The length of a time window may be determined by the number of measuring times in the sequence in the time window in question.

Alternatively or in combination, the incremental extension may be ended if the second significance criterion is exceeded. In this case, the alarm state may additionally be set.

Alternatively or in combination, for each of the evaluation times and optionally for each step of the window extension, it may be checked whether the difference between the height threshold value and the determined fall height exceeds a third significance criterion, for example according to $\lambda - \lambda_{SW} > -s_3$. The third significance criterion may be five times the estimation error. The incremental extension may be ended if the third significance criterion is exceeded.

After the extension has ended, the signal analysis may be continued with an increased evaluation time (for example, increased by a measuring time). The incremental increase in the evaluation time may be implemented as an external loop. The incremental extension of the first time window may be implemented as an internal loop.

According to another aspect, a method for detecting a fall of a person is provided. The method includes a step of capturing a time-dependent air pressure signal that is determined by means of at least one air pressure sensor worn on the body of the person, and a step of determining a fall height with respect to an evaluation time by means of a window-based signal analysis of the time-dependent air pressure signal, the window-based signal analysis including a first time window before the evaluation time and a second time window, which does not overlap with the first time window, after the evaluation time, and the fall height being determined from a difference between a first filter value that is computed based on the time-dependent air pressure signal in the first time window, and a second filter value that is computed based on the time-dependent air pressure signal in the second time window.

The method may also include any functional feature of the device in a corresponding method step.

BRIEF DESCRIPTION OF THE FIGURES

For a comprehensive understanding of the technology described here, exemplary embodiments are described below by way of example, with reference to the appended drawings which show the following.

DETAILED DESCRIPTION OF THE INVENTION

Figure 1:
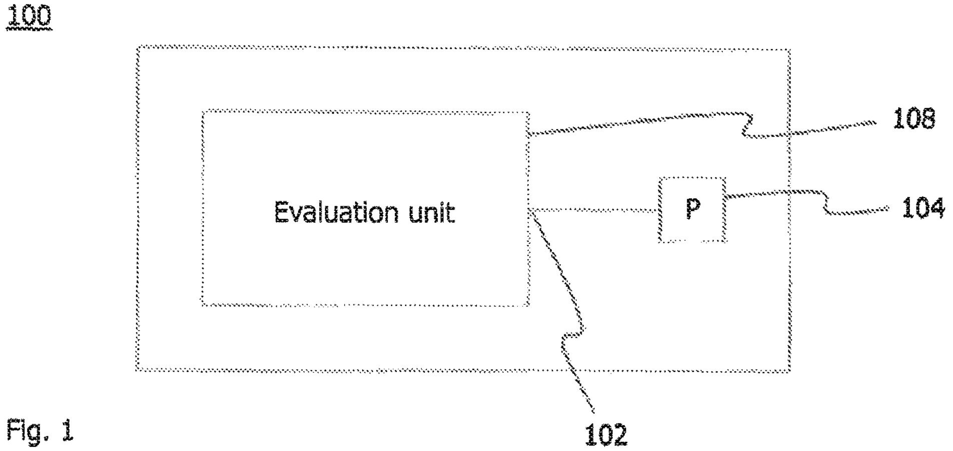
FIG. 1 schematically shows a first exemplary embodiment of a device for detecting a fall using at least one wearable integrated air pressure sensor.

FIG. 1 shows a schematic block diagram of a device, denoted in general by reference numeral 100, for detecting a fall of a person. The first exemplary embodiment shown in FIG. 1 includes an interface 102 within the device 100, to which an air pressure sensor 104 is connected. The device 100 also includes an evaluation unit 108 which analyzes the time dependency of air pressure signals captured by the interface.

Figure 2:
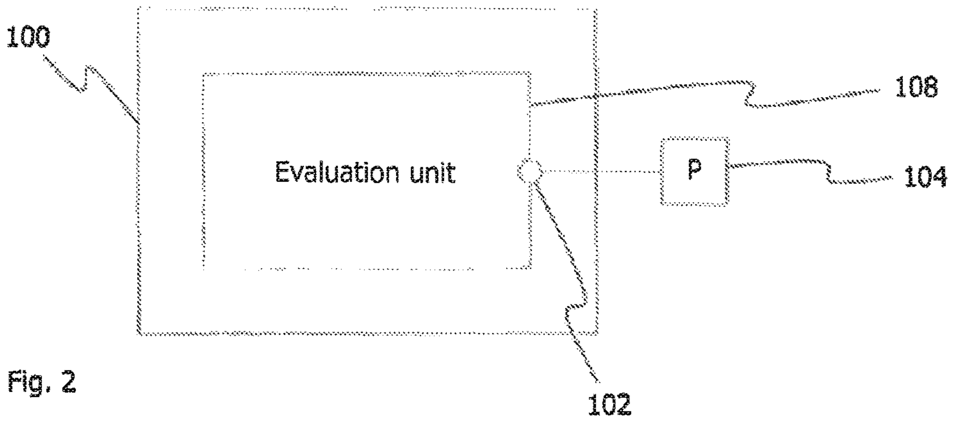
FIG. 2 schematically shows a second exemplary embodiment of a device for detecting a fall using at least one wearable external air pressure sensor.

FIG. 2 shows a schematic block diagram of a second exemplary embodiment of the device 100, in which the air pressure sensor 104 is not part of the device 100. The interface 102 includes a plug-in connection for electrical and mechanical accommodation of the air pressure sensor 104.

Figure 3:
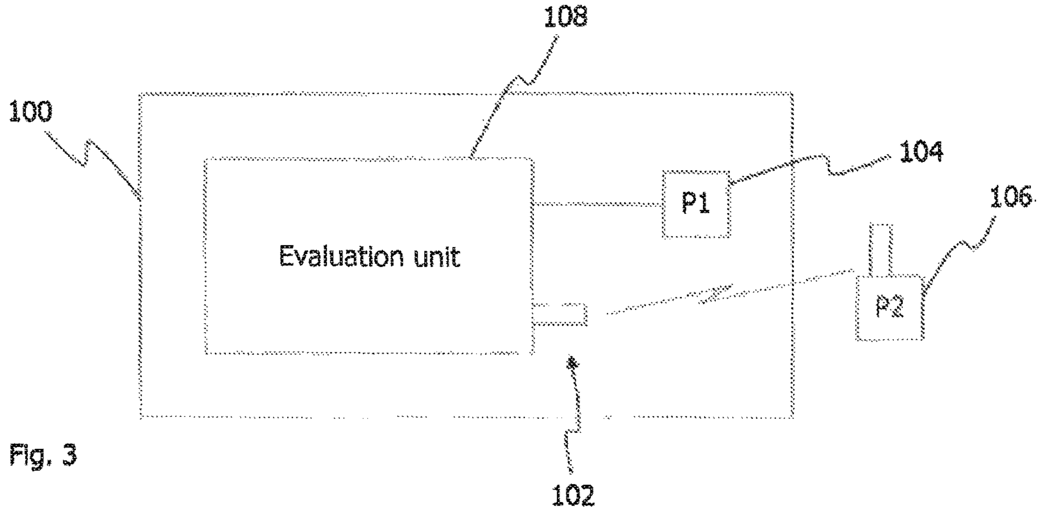
FIG. 3 schematically shows a third exemplary embodiment of a device for detecting a fall using at least one stationary reference air pressure sensor.

A third exemplary embodiment of the device 100 is shown in FIG. 3. The interface 102 captures air pressure signals of an integrated air pressure sensor 104 and of a reference air pressure sensor 106. The evaluation unit 108 and the air pressure sensor 104 are galvanically coupled. The evaluation unit 108 communicates with the reference air pressure sensor 106 via a wireless connection.

At least the air pressure sensor 104 is worn on the body of a person in all three exemplary embodiments of the device 100. The air pressure sensor 104 allows a barometric height measurement, making use of the relationship between static air pressure and height which exists due to gravitational acceleration. In the simplified case of a uniform temperature over the relevant height of a possible fall, there is an exponential relationship between absolute pressure and height, so that a linear relationship may be assumed between small pressure differences due to small height differences. For example, based on a pressure difference $\Delta p$, a fall height $\lambda = -\Delta p \cdot H/p_0$ may be concluded, using the so-called scale height $H = R \cdot T/(g \cdot M)$, where R is the gas constant for dry air having an average molar mass M at an absolute temperature T and a pressure $p_0$ at the selected zero level (for example, the level at which the fall takes place).

While the exemplary embodiments of the device 100 shown in FIGS. 1 to 3 use a worn air pressure sensor 104 for detecting a change in air pressure $\Delta p$ before and after the fall, measured values from multiple worn air pressure sensors 104 may also be detected and averaged, for example, in order to reduce measuring errors or decrease anisotropic pressure influences such as dynamic pressure.

In the case of the third exemplary embodiment in FIG. 3, the detected air pressure signal is based on a difference between the air pressure measured by the worn air pressure sensor 104 and a reference air pressure measured by the reference air pressure sensor 106. The reference air pressure sensor 106 may be stationary, so that the difference between the air pressures measured by the air pressure sensors 104 and 106 eliminates large-scale changes in air pressure. Meanwhile, the physical distance between the worn air pressure sensor 104 and the stationary reference air pressure sensor 106 determines a length scale of the eliminated large-scale fluctuations in air pressure.

Figure 4:
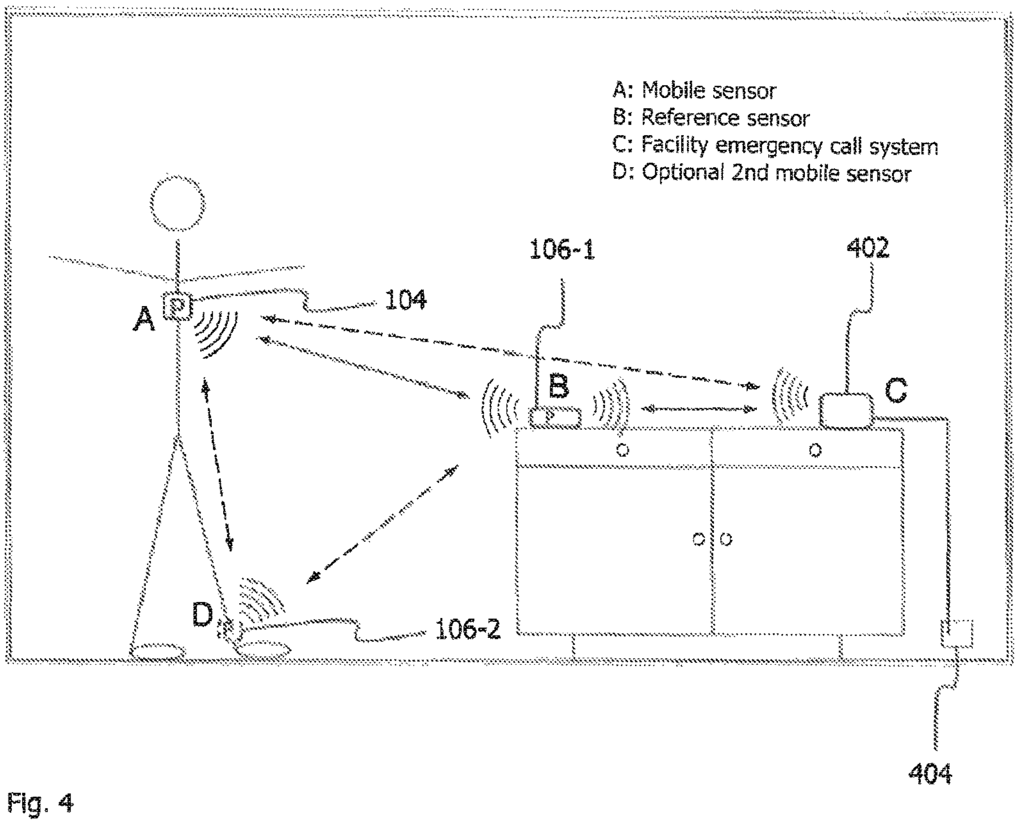
FIG. 4 schematically shows a fourth exemplary embodiment of a device for detecting a fall using multiple mobile air pressure sensors.

FIG. 4 shows one exemplary embodiment of a system 400 for detecting a fall using a worn air pressure sensor 104 and a stationary reference air pressure sensor 106-1. The system 400 also includes a trigger unit 402. The worn air pressure sensor 104, the reference air pressure sensor 106-1, and the trigger unit 402 are in a wireless connection. The wireless connection may be provided in pairs. Alternatively, the reference air pressure sensor 106-1 together with a relay station may form a unit which provides a wireless connection between the trigger unit 402 and the worn air pressure sensor 104.

The device 100 may be situated in a spatial association with each of the components 104, 106-1, or 402. An integration of the device 100 into the trigger unit 402 may be advantageously operated via a power supply, so that the operating lives of the battery-operated components 104 and/or 106-1 are prolonged. For an uninterrupted power supply, the trigger unit 402 may also include an additional battery power supply.

As an alternative or in addition to the reference air pressure sensor 106-1, in one alternative design of the system 400 a reference air pressure sensor 106-2 is situated at a low-level body position. The low-level body position is selected in such a way that in the event of a fall on a flat surface, the reference air pressure sensor 106-2 does not reach a significantly lower location. For a fall on a substantially inclined surface, for example stairs, an immobile position of the reference air pressure sensor 106-2 may be above that of the worn air pressure sensor 104.

In an institutional application (a hospital or nursing home, for example), the trigger unit 402 is connected to a facility emergency call system 404. In a residential application, the trigger unit 402 is connected to a landline network connection 404. Alternatively or for redundancy, the trigger unit 402 is connected to a mobile communications network or a local data communications network (for example, a WLAN according to the IEEE-802.11 standards family).

As an alternative or in addition to the reference air pressure sensors 106-1 and 106-2, a reference air pressure signal of the local atmospheric pressure (in real time, for example) may also be captured by the interface 102 via the landline network connection, the mobile communications network, or the local data communications network.

Figure 5:
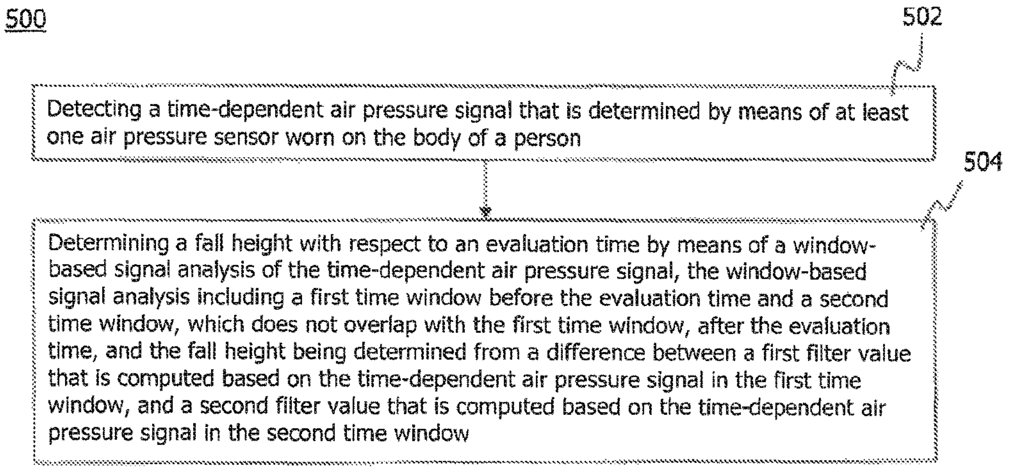
FIG. 5 shows a flow chart of a method for detecting a fall, which is implementable in the devices in FIGS. 1 to 4.

FIG. 5 shows a method 500 for detecting a fall of a person. A time-dependent air pressure signal determined by means of at least one air pressure sensor worn on the body of the person is detected in a step 502 of the method 500. The detected time-dependent air pressure signal may be a difference signal between a worn air pressure sensor and a reference air pressure sensor.

A fall height with respect to an evaluation time is determined in a step 504 of the method 500 by means of a window-based signal analysis of the time-dependent air pressure signal. The window-based signal analysis includes a first time window before the evaluation time and a second time window, which does not overlap with the first time window, after the evaluation time. The fall height is determined from a difference between a first filter value, computed only in the first time window, based on the time-dependent air pressure signal, and a second filter value, computed only in the second time window, based on the time-dependent air pressure signal.

The method 500 is carried out by the device 100. The detected time-dependent air pressure signal may be provided by any of the worn air pressure sensors 104, or may be a difference signal based on the worn air pressure sensor 104 and the reference air pressure sensor 106.

Figure 6A:
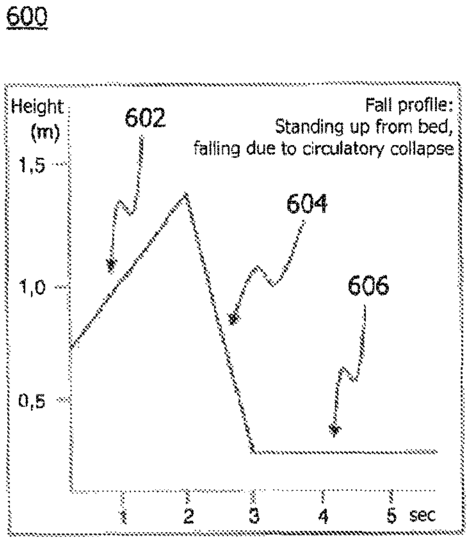
FIGS. 6A and 6B show examples of curves of an air pressure signal.
Figure 6B:
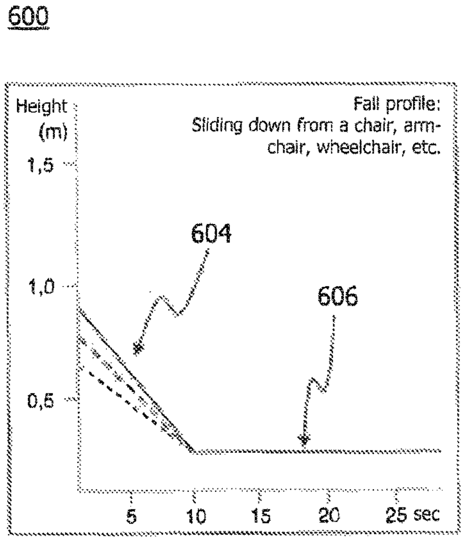

FIGS. 6A and 6B schematically show two examples of the time-dependent air pressure signal. Due to the assumed relationship between the change in air pressure and the change in height, the time-dependent air pressure signal 600 is plotted in height units on the vertical axis. The time-dependent air pressure signal 600 may basically be divided into a movement phase 602, a range 604 of the actual falling process, and an immobile phase 606. The window-based signal analysis by the evaluation unit 108 according to step 504 computes the first filter value based on the movement phase, and computes the second filter value based on the immobile phase 606, with masking of the fall range 604 when the evaluation time in question coincides with the time of the fall.

In the first example of the time-dependent air pressure signal 600 shown in FIG. 6A, in the movement phase 602 a person rises from a lying position on a bed surface to a sitting position on an edge of the bed, and upon attempting to stand up from the bed loses his/her balance or even loses consciousness, for example due to temporary insufficient blood circulation in the brain. The falling motion ends in the immobile phase 606 on a floor surface.

In the second example of the time-dependent air pressure signal 600 shown in FIG. 6B, the body slides from the lying or sitting position to a lower level. The sliding movement is part of the falling range 604, and the end position at the lower level is part of the immobile phase 606, of the time-dependent air pressure signal 600.

Typical sitting heights are approximately 0.50 m on a bed or an office chair, for example, and 0.44 m on an armchair or a kitchen chair, for example. When the worn air pressure sensor 104 is attached at chest level, a fall height detected by the worn air pressure sensor 104 increases as a function of the body height.

Figure 7:
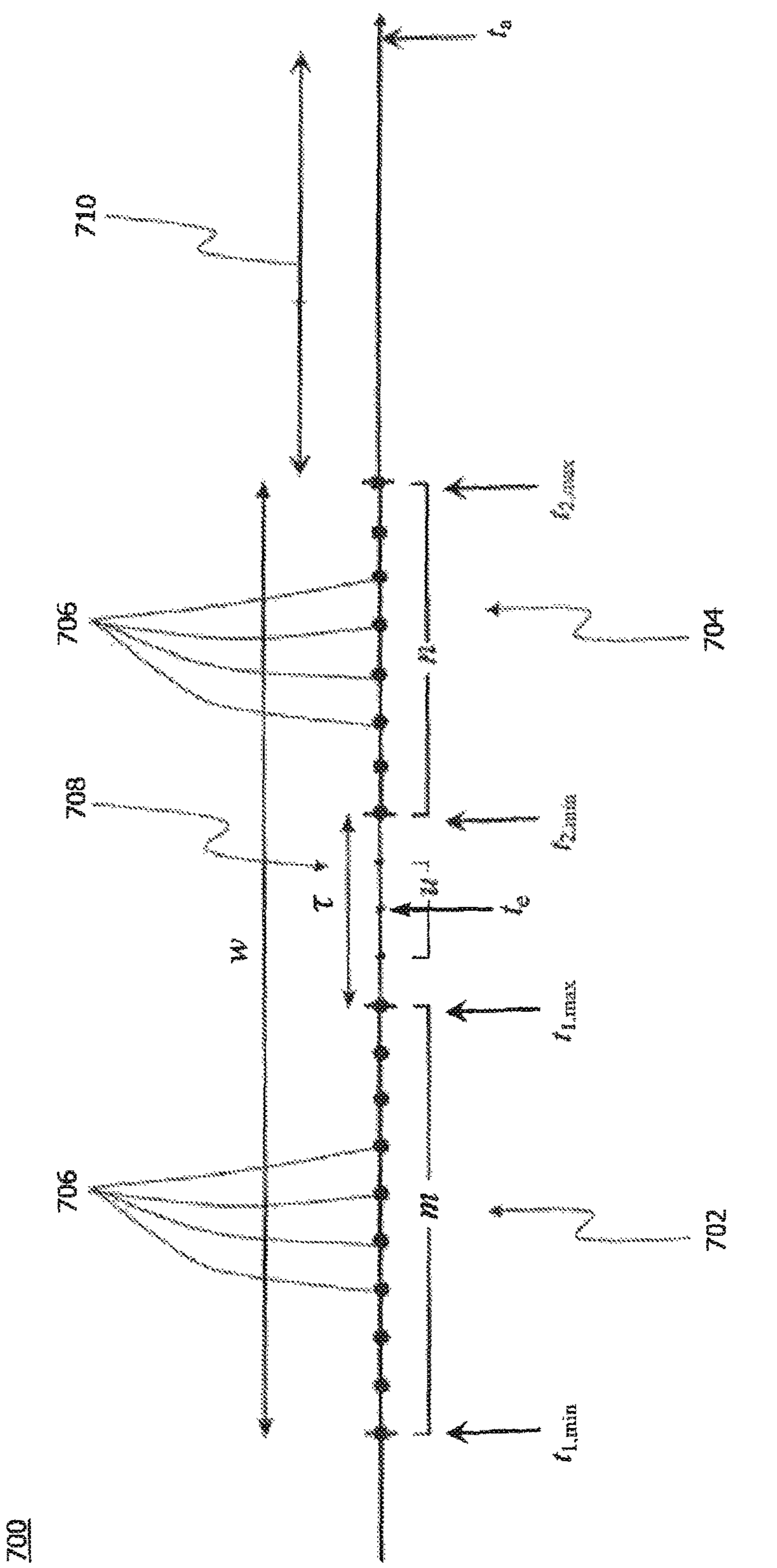
FIG. 7 schematically shows a first time window and a second time window for a window-based signal analysis according to the method in FIG. 5.

FIG. 7 schematically shows the window-based signal analysis 504 of the time-dependent air pressure signal 600. An overall time window w of the signal analysis 504 includes the first time window 702 and the second time window 704. The time period w may be 120 seconds, for example. The time windows 702 and 704 are sliding windows. The signal analysis takes place cyclically or in packets.

The first time window 702 includes m measuring times 706 of the detected air pressure signal. The second time window 704 includes n measuring times of the detected air pressure signal. The measuring times may be spaced at intervals of 1 second, for example.

The first time window 702 and the second time window 704 are separated by an interval 708 having the maximum assumed fall duration τ. For example, the nominal time of the fall event in the middle of the interval 708 may be defined as the evaluation time $t_e$.

In addition to the measuring times N=m+n on which the signal analysis is based, the u measuring times in the interval 708 are not taken into account in the window-based signal analysis 504 with regard to the evaluation time $t_e$. For a continuous evaluation (also referred to as online evaluation), the current time stamp $t_a$ may coincide with the upper limit $t_{2,max}$ of the second time window 704. Alternatively, there may be a delay time 710 between the second time interval 704 and the current time stamp during the signal analysis, for example due to a time for data preparation and/or data transmission.

In one exemplary embodiment of the signal analysis 504, a minimum time interval between the evaluation time $t_e$ and the current time stamp $t_a$ is predefined in order to establish a minimum quiescent time having an essentially constant air pressure signal 600 as an additional condition for triggering an alarm, for example via an incremental increase of the first time window 702 and/or of the second time window 704. The initial use of shorter time windows reduces the analytical effort, and thus, the requirements for memory, computing power, and power consumption.

The signal analysis 504 may be carried out in the first time window 702 and/or in the second time window 704 by means of different polynomial degrees. The signal analysis 504, beginning with a low polynomial degree, for example zero-degree, may be advanced to higher polynomial degrees, for example until a significant fall height is established or a maximum polynomial degree is reached. The window size may be a function of the polynomial degree; for example, the window size may increase with the polynomial degree.

Alternatively or additionally, the window size may be determined by a predefined accuracy according to the estimation error. For example, a covariance matrix may be determined in the course of a fit. The estimation error may be computed based on the covariance matrix and a theoretical accuracy value of the sensor. The latter estimation error is also referred to as the theoretical estimation error. Alternatively or in combination, the estimation error may be computed based on the covariance matrix and the sum of the quadratic deviations of the fit, for example as the product of a diagonal element of the covariance matrix and the square root of the sum of the quadratic deviations. The sum of the quadratic deviations of the fit may be normalized, for example, by dividing by the number of measuring times minus the number of degrees of freedom of the fit. The latter results in an estimation error of the instantaneous signal analysis 504.

The air pressure at a given location is not constant over time. It is influenced primarily by meteorological balancing processes. Corresponding to the relationship between air pressure and height, these ongoing changes in the air pressure may result in apparent changes in height of up to 30 to 40 m per hour. In addition, the air pressure at a fixed location is subject to periodic changes over the day, for example due to diurnal variations in the air temperature and natural oscillation of the earth's atmosphere. Apparent changes in height at a rate of approximately 2 to 5 m per hour correspond to the periodic changes.

Since during a barometric height measurement the weather conditions are generally superimposed on the time-dependent air pressure signal 600 to be measured, a time dependency of the air pressure signal 600 in the first time window 702 and/or in the second time window 704 is compensated for.

Figure 8A:
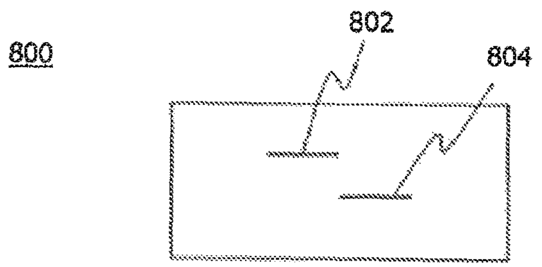
FIGS. 8A to 8C show schematic time dependencies for uniformly compensating for a time dependency of the air pressure signal in the first time window and in the second time window in FIG. 7.
Figure 8B:
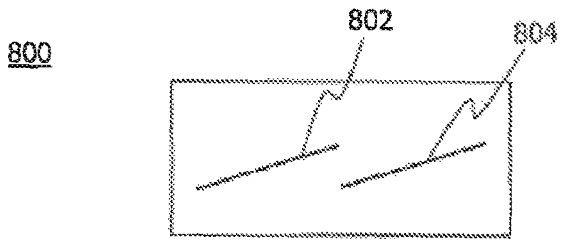
Figure 8C:
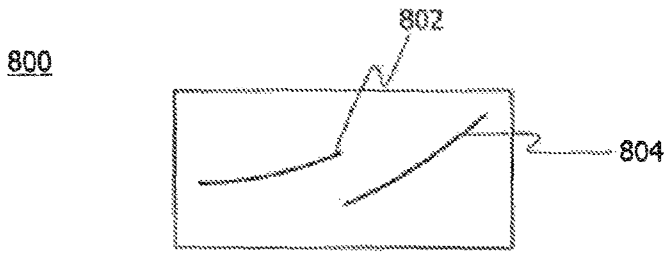

FIGS. 8A to 8C schematically show a time dependency 800, whose segment 802 in the first time window 702 and whose segment 804 in the second time window 704 are adapted to the detected time-dependent air pressure signal 600 by compensation computation methods. The weather trend in the time-dependent air pressure signal 600 may thus be compensated for in the course of determining the first and second filter values. The compensation is based on a uniform time dependency F(t) for both time windows 702 and 704, which differ solely by an offset value ΔC corresponding to the estimated fall height λ. For example, the time dependency 800 may include a polynomial or Fourier expansion.

The function M(t) to be fitted is adapted to the detected air pressure signal 600, taking into account the m measuring times in the first time window 702 and the n measuring times in the second time window 704:

$$M(t)=\begin{cases}F(t)+C_1 & \text{in the first time window 702}\\ F(t)+C_2 & \text{in the second time window 704}\end{cases}$$

The fall height λ is deduced from the pressure jump $\Delta C=C_2-C_1$. The function M(t) may also be represented as the sum of the uniform time dependency F(t) and a jump function $\Theta(t-t_e)$ with a step at time $t_e$.

The uniform time dependency 800 for both time windows 702 and 704 is a linear and/or quadratic function of time t:

$$F(t)=a_1\cdot t+a_2\cdot t^2.$$

The case in FIG. 8A corresponds to the parameter setting $a_1=a_2=0$, i.e., no compensation for a time dependency. Only the offset values $C_1$ and $C_2$ are fit parameters.

FIG. 8B schematically shows the compensation for an exclusively linear time dependency 800; i.e., $a_2=0$ is not a fit parameter. Only the coefficient $a_1$ and the offset values $C_1$ and $C_2$ (or their difference) are fit parameters.

FIG. 8C schematically shows a compensation for the time dependency 800 to the second order in time. The compensation computation includes the fit parameters $C_1$, $C_2$, $a_1$, and $a_2$ or $C_1$, $\Delta C=C_2-C_1$, $a_1$, and $a_2$.

Figure 9A:
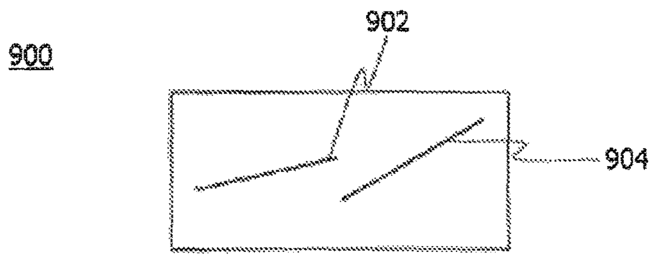
FIGS. 9A and 9B show schematic time dependencies for independently compensating for a time dependency of the air pressure signal in the first time window and in the second time window in FIG. 7.
Figure 9B:
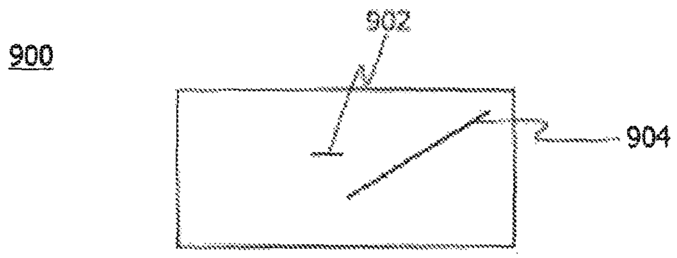

FIGS. 9A and 9B show schematic time dependencies 900 which are adapted, independently of one another in the first time window 702 and in the second time window 704, to the detected time-dependent air pressure signal 600. The first time dependency 902, is adapted, based on the m measuring times of the first time window 702, independently from the adaptation of a second time dependency 904 based on the n measuring times in the second time interval 704.

Based on the function which is adapted to the detected air pressure signal 600, $$M(t)=\begin{cases}F_1(t) & \text{in the first time window 702}\\ F_2(t) & \text{in the second time window 704}\end{cases},$$

the fall height λ is deduced from the pressure jump $F(t_{2,min})-F(t_{1,max})$.

The time dependencies 902 and 904 for the time windows 702 and 704, respectively, are linear and/or quadratic functions of time t:

$$F_i(t)=a^{(i)}{}_0+a^{(i)}{}_1\cdot t+a^{(i)}{}_2\cdot t^2 \text{ for } i=1,2.$$

The compensation computation includes the fit parameters $a^{(1)}{}_0$, $a^{(1)}{}_1$, $a^{(1)}{}_2$, $a^{(2)}{}_1$, and $a^{(2)}{}_2$.

The compensation shown in FIG. 9A eliminates a time dependency 900, which is linear in time, in the two time windows 702 and 704; i.e., the quadratic coefficients $a^{(i)}{}_2=0$ are not fit parameters.

The compensation shown in FIG. 9B eliminates only a linear time dependency 904 in the second time window 704; i.e., $a^{(1)}{}_1=0$ is additionally set.

Together with the estimated value for the fall height λ obtained from the compensation computation, the compensation computation results in a theoretical or estimated estimation error $\sigma_\lambda$ of the fall height λ. This signal analysis 504 is carried out for each evaluation time $t_e$.

In a first embodiment variant, the estimation error $\sigma_\lambda$ is computed from the square root of the sum of the quadratic deviations between the fitted time dependency M(t) and the time-dependent air pressure signal. The sum includes the N=m+n quadratic deviations in the first time window 702 and in the second time window 704.

In a second embodiment variant, the estimation error is computed from the standard deviation a of the detected air pressure signal according to $$\sigma_\lambda=\sigma\cdot(1/m+1/n)^{1/2}.$$

Optionally, a first significance criterion $z_1$ is determined from the estimated fall height λ and the estimation error $\sigma_\lambda$:

$$z_1=|\lambda|/\sigma_\lambda.$$

If $z_1$ is not greater than 2, for example, the estimated value does not reach the significance level α=4.55%. The signal analysis is then ended at this evaluation time, without changing an alarm state.

However, if the estimated fall height λ meets a second significance criterion $$z_2=(\lambda-\lambda_{SW})/\sigma_\lambda,$$

where $z_2>3$ for a threshold value $\lambda_{SW}$, the minimum fall height $\lambda_{SW}$ has been exceeded with a sufficient level of significance, and an alarm state is set.

In an enhanced exemplary embodiment of the analysis 504, not just a fall height and an associated estimation error with regard to each evaluation time $t_e$ are determined. In addition, for a given evaluation time, starting from a minimum window size (which includes, for example, $m_{min}=2$ measuring times), the window size of the first time window 702 is incrementally increased by adding earlier measuring times 706.

The fall height λ and the associated estimation error $\sigma_\lambda$ are determined for each increased first time window 702. The first time window 702 is incrementally increased until a maximum window size ($m_{max}=320$, for example) is reached, or optionally until the second significance criterion $z_2$ falls below a lower limit (according to $z_2<-5$, for example), or until a fall is detected (due to $z_2>3$, for example).

As an alternative or in addition to the incremental increase in the first time window 702, in the alarm state the second time window 704 may be shifted in time as a sliding second time window 704, independently of the first time window 702. For example, upon entry into an alarm state, an alarm signal is not immediately output by the device 100 or the trigger unit 402. In the alarm state, initially the second time window 704 is shifted toward longer measuring times 706. Optionally, the end time $t_{1,max}$ of the first time window 702 may be shifted toward longer measuring times 706 if the shift results in an increase in the height value corresponding to the end time of the first time window 702 ($F(t_{1,max})$). The end time $t_{1,max}$ of the first time window 702 may be set to the maximum height value. The start time $t_{1,min}$, for example, remains unchanged.

For each shifted second time window, a quality Q of the fit of the time dependency 804 or 904 is determined in the second time window 704. Alternatively, a Chow test may be performed, in which in a first embodiment variant the distribution in the first time window 702 and the second time window 704 is maintained, or in a second embodiment variant only the second time window 704 having an appropriate distribution is examined for a so-called structural break.

If the quality Q meets a threshold value $Q_{SW}$ when the predefined minimum time interval between the current time stamp $t_a$ and the evaluation time $t_e$ is reached, an alarm signal is output.

The triggering of the alarm may take place, for example, within 60 to 90 seconds after the actual fall, at time $t_e$. A response by the person to prevent the alarm may thus be recognized. The trigger unit 402 may allow a pre-alarm with a cancellation option before being automatically relayed to an emergency call, for example to exclude lying down intentionally.

The signal analysis 504 by means of the uniform time dependency 800 is also referred to as template analysis (TA), and is abbreviated as TA0, TA1, and TA2, with an indication of the polynomial degree (for the cases shown in FIGS. 8A, 8B, and 8C).

The signal analysis 504 by means of two time dependencies 902 and 904 is also referred to as gap analysis (GA), and is abbreviated as GA1 (for the case in FIG. 9A) and GA-0-1 (for the case in FIG. 9B), with addition of the corresponding polynomial degree.

To reach a predefined theoretical estimation error (theoretical accuracy) of 2.5 cm, for example, the first time window 702 and the second time window 704 may each include 32 measuring times for the signal analysis 504 according to TA0, 128 measuring times for the signal analysis 504 according to TA1 and TA2, and 227 measuring times for the signal analysis 504 according to TA3. The minimum time interval between the evaluation time $t_e$ and the current time stamp $t_a$ may be selected corresponding to the maximum polynomial degree to be evaluated.

Detailed measurement series have resulted in reliable fall recognitions when the signal analyses 504 marked by "x" below are implemented:

| Signal analysis 504 | TA0 | TA1 | TA2 | GA1 | GA-0-1 |
|---|---|---|---|---|---|
| Method accuracy $\sigma_\lambda$ (cm) | 2.5 | 2.5 | 2.5 | 2.5 | 4.8 |
| Fall height: 1.04 m, threshold value $\lambda_{SW}$ = 0.50 m | x | x | x | x | x |
| Fall height: 0.59 m, threshold value $\lambda_{SW}$ = 0.44 m | x | x | x | x | |
| Fall height: 0.50 m, threshold value $\lambda_{SW}$ = 0.35 m | x | x | x | x | |
| Fall after standing up quickly (FIG. 6A) | | | | | x |

The column headers contain the abbreviations of the implementation of the signal analysis 504. An air pressure sensor 104 was used, with the method accuracy $\sigma_\lambda$ given in centimeters. The reliably recognized fall height and the threshold value are provided at the left in the above table.

In an enhanced exemplary embodiment of the device 100, a temperature sensor worn on the body is also provided. The output of an alarm signal may be coupled to the additional condition that the temperature sensor detects a drop in temperature. The temperature sensor may be thermally decoupled from the body, for example by a thermal insulation layer.

Figure 10:
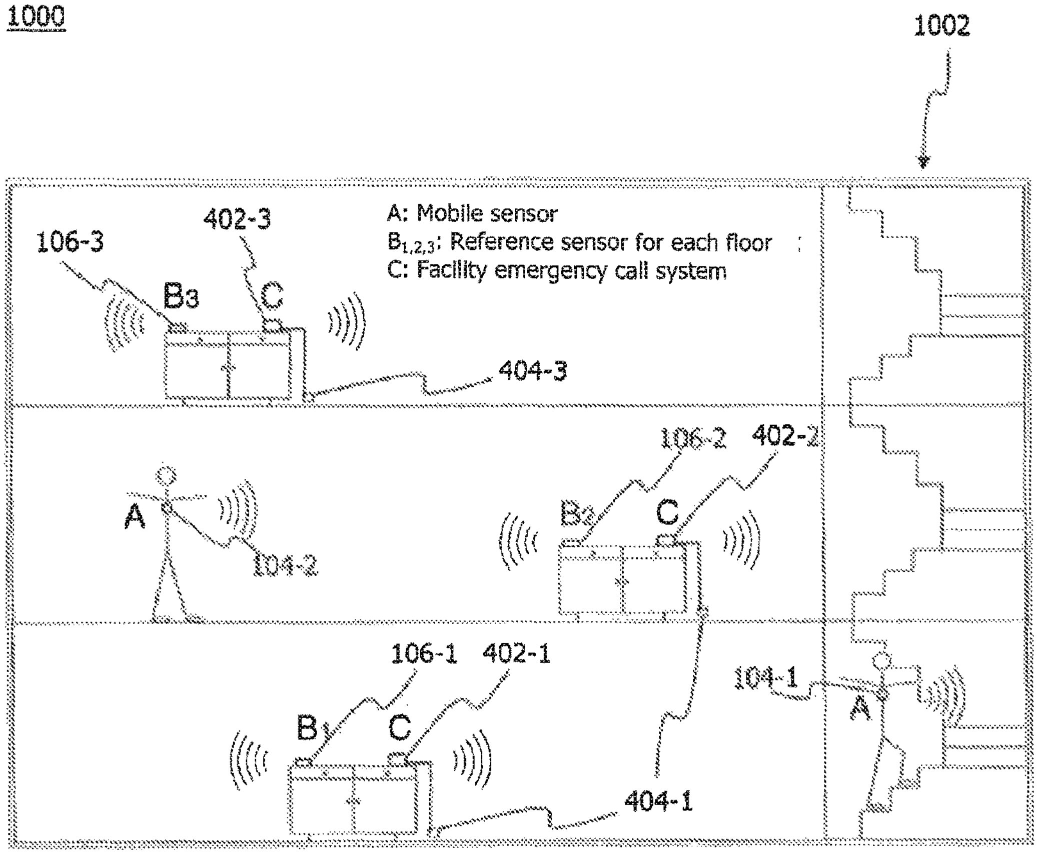
FIG. 10 shows a system for detecting a fall using multiple spatially distributed stationary reference air pressure sensors.

FIG. 10 shows an expanded system 1000 having at least one device 100 for detecting a fall of a person and multiple reference air pressure sensors. The system 1000 extends over multiple floors, which are accessible by stairs 1002 and/or elevator. A reference air pressure sensor 106-1, 106-2, and 106-3 is situated on each floor. Depending on a signal strength of the air pressure signal captured by the worn air pressure sensor 104-1 or 104-2, the device 100 carries out the method 500 in a spatially associated trigger unit of the trigger units 402-1 and 402-2. For example, the device 100 in the trigger unit 402-1 carries out the method 500 based on the worn air pressure sensor 104-1 associated with it, taking the reference air pressure sensor 106-1 into account. If a person wearing the air pressure sensor 104-1 goes from the first floor to the second floor, the device 100 integrated into the trigger unit 402-2 takes over carrying out the method 500 based on the worn air pressure sensor 104-1, and taking the reference air pressure sensor 106-2 into account.

At least in individual exemplary embodiments, the described technology for detecting a fall allows reliable recognition of a fall without specifying a certain fall pattern. External influences, such as large-scale pressure fluctuations due to changes in weather, may be eliminated by compensating for a corresponding time dependency, and/or by a reference air pressure sensor being taken into account by the signal analysis. False alarms may thus be prevented at low threshold values for reliable recognition of falls of a person.

The invention claimed is:

1. A device (100) for detecting a fall of a person, comprising:

an interface (102) which is designed for capturing a time-dependent air pressure signal (600) that is determined by means of at least one air pressure sensor (104; 104, 106; 104, 106-1, 106-2) worn on the body of the person, and an evaluation unit (108) which is designed for determining a fall height (λ) with respect to an evaluation time ($t_e$) by means of a window-based signal analysis of the time-dependent air-pressure signal, wherein the window-based signal analysis includes a first time window (702) before the evaluation time and a second time window (704), which does not overlap with the first time window, after the evaluation time, and wherein the fall height is determined from a difference between a first filter value that is computed based on the time-dependent air pressure signal in the first time window, and a second filter value that is computed based on the time-dependent air pressure signal in the second time window;

wherein the time-dependent air pressure signal (600) includes a sequence of values associated in each case with a measuring time (706), and the fall height (λ) is determined with respect to a plurality of evaluation times by incrementally shifting the evaluation time ($t_e$), the first time window (702), and the second time window (704) by a measuring time of the sequence, to later points in time, and the fall height is determined for each of the evaluation times.

2. The device according to claim 1, wherein the air pressure signal (600) is periodically sampled, and the first time window (702) is temporally separate from the second time window (704) by at least one sampling period.

3. The device according to claim 1, wherein the determination of the fall height disregards the time-dependent air pressure signal (600) between the first time window (702) and the second time window (704).

4. The device according to claim 1, wherein the first filter value and/or the second filter value are/is an average value of the time-dependent air pressure signal.

5. The device according to claim 1, wherein the computation of the first filter value or of the second filter value compensates for a time dependency (800; 900) of the time-dependent air pressure signal.

6. The device according to claim 5, wherein the time dependencies (900) for the first time window (702) and for the second time window (704) are each compensated for independently of one another.

7. The device according to claim 5, wherein in the first time window (702) a first time dependency (902; $F_1(t)$) is fitted to the time-dependent air pressure signal, and in the second time window a second time dependency (904; $F_2(t)$) is fitted to the time-dependent air pressure signal, the fall height being determined from the difference between the first time dependency ($F_1(t_{1,max})$) at the end time of the first time window, and the second time dependency ($F_2(t_{2,min})$) at the start time of the second time window.

8. The device according to claim 5, wherein for the first time window (702) and for the second time window (704) the same time dependency (800) is compensated for.

9. The device according to claim 5, wherein in the first time window, the time dependency (802; F(t)), having a first time-independent offset value ($C_1$) as a fit parameter, is fitted to the time-dependent air pressure signal, and in the second time window, the same time dependency (804; F(t)), having a second time-independent offset value ($C_2$) as a fit parameter, is fitted to the time-dependent air pressure signal, the fall height being determined from the difference between the first offset value and the second offset value.

10. The device according to claim 1, wherein for each of the evaluation times, it is checked whether the determined fall height exceeds a first significance criterion ($z_1$).

11. The device according to claim 1, wherein for each of the evaluation times, it is checked whether the difference between the determined fall height and a height threshold value exceeds a second significance criterion ($z_2$).

12. The device according to claim 11, wherein an alarm state is set if the second significance criterion ($z_2$) is exceeded.

13. The device according to claim 12, further comprising a trigger unit (402) which is designed for outputting an alarm signal if, in the alarm state, a fit of the time-dependent air pressure signal in the second time window exceeds a predefined quality criterion (Q).

14. The device according to claim 11, wherein for each evaluation time ($t_e$), the first time window (702) is incrementally extended toward earlier measuring times (706) until a maximum length of the first time window (702) is reached, until the second significance criterion ($z_2$) is exceeded, or until the determined fall height falls below the height threshold value by a third significance criterion ($z_3$).

15. The device according to claim 1, wherein the device further comprises a temperature sensor which is worn on the body and thermally decoupled from the body, and wherein an alarm signal is outputted only if the temperature sensor detects a drop in temperature.

16. A device (100) for detecting a fall of a person, comprising:

an interface (102) which is designed for capturing a time-dependent air pressure signal (600) that is determined by means of at least one air pressure sensor (104; 104, 106; 104, 106-1, 106-2) worn on the body of the person, and an evaluation unit (108) which is designed for determining a fall height (λ) with respect to an evaluation time ($t_e$) by means of a window-based signal analysis of the time-dependent air-pressure signal, wherein the window-based signal analysis includes a first time window (702) before the evaluation time and a second time window (704), which does not overlap with the first time window, after the evaluation time, and wherein the fall height is determined from a difference between a first estimation value that is computed based on the time-dependent air pressure signal in the first time window, and a second estimation value that is computed based on the time-dependent air pressure signal in the second time window;

wherein the computation of the first estimation value or of the second estimation value compensates for a time dependency (800; 900) of the time-dependent air pressure signal; and wherein at least one of:

in the first time window (702) a first time dependency (902; $F_1(t)$) is fitted to the time-dependent air pressure signal, and in the second time window a second time dependency (904; $F_2(t)$) is fitted to the time-dependent air pressure signal, the fall height being determined from the difference between the first time dependency ($F_1(t_{1,max})$) at the end time of the first time window, and the second time dependency ($F_2(t_{2,min})$) at the start time of the second time window; and in the first time window, the time dependency (802; F(t)), having a first time-independent offset value ($C_1$) as a fit parameter, is fitted to the time-dependent air pressure signal, and in the second time window, the same time dependency (804; F(t)), having a second time-independent offset value ($C_2$) as a fit parameter, is fitted to the time-dependent air pressure signal, the fall height being determined from the difference between the first offset value and the second offset value.

17. A device for detecting a fall of a person, the device comprising:

an interface capturing a time-dependent air pressure signal that is determined using at least one air pressure sensor worn on the body of the person;

and an evaluation unit that determines a fall height (λ) with respect to an evaluation time ($t_e$) using a window-based signal analysis of the time-dependent air-pressure signal, wherein the window-based signal analysis includes a first time window (702) before the evaluation time and a second time window (704), which does not overlap with the first time window, after the evaluation time, and wherein the fall height is determined from a difference between a first filter value computed based on the time-dependent air pressure signal in the first time window, and a second filter value computed based on the time-dependent air pressure signal in the second time window;

wherein in the first time window (702) a first time dependency (902; $F_1(t)$) is fitted to the time-dependent air pressure signal, and in the second time window a second time dependency (904; $F_2(t)$) is fitted to the time-dependent air pressure signal, the fall height being determined from the difference between the first time dependency ($F_1(t_{1,max})$) at the end time of the first time window, and the second time dependency ($F_2(t_{2,min})$ at the start time of the second time window.

18. A device for detecting a fall of a person, the device comprising:

an interface capturing a time-dependent air pressure signal that is determined using at least one air pressure sensor worn on the body of the person; and an evaluation unit that determines a fall height (λ) with respect to an evaluation time ($t_e$) using a window-based signal analysis of the time-dependent air-pressure signal, wherein the window-based signal analysis includes a first time window (702) before the evaluation time and a second time window (704), which does not overlap with the first time window, after the evaluation time, and wherein the fall height is determined from a difference between a first filter value computed based on the time-dependent air pressure signal in the first time window, and a second filter value computed based on the time-dependent air pressure signal in the second time window;

wherein the computation of the first filter value or of the second filter value compensates for a time dependency (800; 900) of the time-dependent air pressure signal;

wherein in the first time window, the time dependency (802; F(t)), having a first time-independent offset value ($C_1$) as a fit parameter, is fitted to the time-dependent air pressure signal, and in the second time window, the same time dependency (804; F(t)), having a second time-independent offset value ($C_2$) as a fit parameter, is fitted to the time-dependent air pressure signal, the fall height being determined from the difference between the first offset value and the second offset value.

* * * * *